United States Patent
Mastroianni

(10) Patent No.: US 9,233,917 B2
(45) Date of Patent: *Jan. 12, 2016

(54) PREPARATION OF NITRILES FROM ETHYLENICALLY UNSATURATED COMPOUNDS

(75) Inventor: Sergio Mastroianni, Lyons (FR)

(73) Assignee: INVISTA NORTH AMERICA S.A R.L., Wilmington, DE (US)

( * ) Notice: Subject to any disclaimer, the term of this patent is extended or adjusted under 35 U.S.C. 154(b) by 460 days.

This patent is subject to a terminal disclaimer.

(21) Appl. No.: 12/999,336

(22) PCT Filed: Jun. 5, 2009

(86) PCT No.: PCT/EP2009/056916
§ 371 (c)(1),
(2), (4) Date: Jan. 27, 2011

(87) PCT Pub. No.: WO2009/153171
PCT Pub. Date: Dec. 23, 2009

(65) Prior Publication Data
US 2011/0166376 A1    Jul. 7, 2011

(30) Foreign Application Priority Data

Jun. 17, 2008  (FR) ..................... 08 03374

(51) Int. Cl.
C07C 255/04 (2006.01)
C07C 253/10 (2006.01)
B01J 31/24 (2006.01)
B01J 31/18 (2006.01)

(52) U.S. Cl.
CPC ............. *C07C 253/10* (2013.01); *B01J 31/185* (2013.01); *B01J 31/2404* (2013.01); *B01J 2231/32* (2013.01); *B01J 2531/847* (2013.01)

(58) Field of Classification Search
CPC ....... C07C 255/04; C07C 253/10; B01J 31/24
USPC ........................................................ 558/338
See application file for complete search history.

(56) References Cited

U.S. PATENT DOCUMENTS

| | | |
|---|---|---|
| 3,496,215 A | 2/1970 | Drinkard, Jr. et al. |
| 3,496,217 A | 2/1970 | Drinkard, Jr. et al. |
| 3,496,218 A | 2/1970 | Drinkard, Jr. et al. |
| 3,631,191 A | 12/1971 | Kane et al. |
| 3,655,723 A | 4/1972 | Drinkard et al. |
| 3,694,485 A | 9/1972 | Drinkard, Jr. et al. |
| 3,766,231 A | 10/1973 | Gosser et al. |
| 3,766,237 A | 10/1973 | Chia et al. |
| 3,773,809 A | 11/1973 | Walter |
| 3,864,380 A | 2/1975 | King et al. |
| 4,082,811 A | 4/1978 | Shook, Jr. |
| 4,339,395 A | 7/1982 | Barnette et al. |
| 4,416,825 A | 11/1983 | Ostermaier |
| 4,774,353 A | 9/1988 | Hall et al. |
| 4,874,884 A | 10/1989 | McKinney et al. |
| 5,512,696 A | 4/1996 | Kreutzer et al. |
| 5,693,843 A | 12/1997 | Breikss et al. |
| 5,847,191 A | 12/1998 | Bunel et al. |
| 5,981,772 A | 11/1999 | Foo et al. |
| 6,048,996 A | 4/2000 | Clarkson et al. |
| 6,127,567 A | 10/2000 | Garner et al. |
| 6,153,758 A | 11/2000 | Sannicolo et al. |
| 6,521,778 B1 | 2/2003 | Fischer et al. |
| 6,770,770 B1 | 8/2004 | Baumann et al. |
| 7,084,293 B2 | 8/2006 | Rosier et al. |
| 7,098,358 B2 | 8/2006 | Burattin et al. |
| 7,105,696 B2 | 9/2006 | Burattin et al. |
| 7,442,825 B2 | 10/2008 | Galland et al. |
| 7,470,805 B2 | 12/2008 | Rosier et al. |
| 7,485,741 B2 | 2/2009 | Bourgeois et al. |
| 7,550,407 B2 | 6/2009 | Bartsch et al. |
| 7,612,223 B2 | 11/2009 | Rosier et al. |
| 7,777,068 B2 | 8/2010 | Bartsch et al. |
| 2004/0116713 A1 | 6/2004 | Beller et al. |
| 2006/0258874 A1 | 11/2006 | Bartsch et al. |
| 2009/0227801 A1 | 9/2009 | Ahlers et al. |
| 2011/0021804 A1 | 1/2011 | Mastroianni |
| 2011/0118499 A1 | 5/2011 | Mastroianni |

(Continued)

FOREIGN PATENT DOCUMENTS

| | | |
|---|---|---|
| DE | 199 53 058 A1 | 5/2001 |
| DE | 103 14 761 A1 | 10/2004 |
| EP | 0 336 314 A2 | 10/1989 |

(Continued)

OTHER PUBLICATIONS

International Search Report corresponding to PCT/EP 2009/056916.
"Aliphatic Compounds" IUPAC Compendium of Chemical Terminology 2nd Edition (1997).
Gibson et al., "Formation and Unexpected Catalytic Reactivity of Oranoaluminum Boryloxides," *Inorg. Chem.*, 40(5): 826-827 (2001).
Hirano et al. (Chem. Commun., 2008, 3234-3241).
Oishi (Silicon(IV) Lewis Acids, in Lewis Acids in Organic Syth., 2000, ch. 9, p. 355-393).
Serwatowski et al., "New Tetrameric Alkylmetal Boryloxides [(μ$^3$-R$_2$BO)MR']$_4$ of Zinc and Cadmium with Heterocubane Structure," *Inorg. Chem.*, 38(22): 4937-4941 (1999).
Serwatowski et al., "Diverse Reactivity of Dialkylaluminum Dimesitylboryloxides [(μMes$_2$BO)AlR$_2$]$_2$. Synthetic and Structural Study," *Inorg. Chem.*, 39(25): 5763-5767 (2000).

(Continued)

*Primary Examiner* — Nyeemah A Grazier
(74) *Attorney, Agent, or Firm* — Robert B. Furr, Jr.; Jeffrey Freeman

(57) ABSTRACT

A process for the hydrocyanation of a hydrocarbon-based compound having at least one site of ethylenic unsaturation into a nitrile compound includes reaction thereof, in a liquid medium, with hydrogen cyanide in the presence of a catalyst containing a metal element selected from among the transition metals and an organophosphorus ligand, wherein the organophosphorus ligand is a mixture of at least one monodentate organophosphite compound and at least one monodentate organophosphine compound; the subject process is especially useful for the synthesis of adiponitrile from butadiene.

19 Claims, No Drawings

(56) References Cited

U.S. PATENT DOCUMENTS

| | | |
|---|---|---|
| 2011/0166376 A1 | 7/2011 | Mastroianni |
| 2011/0288327 A1 | 11/2011 | Mastroianni |

FOREIGN PATENT DOCUMENTS

| | | | |
|---|---|---|---|
| FR | 1 529 134 A1 | | 5/1968 |
| FR | 2 069 411 A1 | | 9/1971 |
| FR | 2 523 974 A1 | | 9/1983 |
| FR | 2830530 A1 | | 4/2003 |
| FR | 2849027 A1 | | 6/2004 |
| FR | 2854892 A1 | * | 11/2004 |
| FR | 2 845 379 A1 | | 4/2009 |
| WO | WO 96/22968 | | 8/1996 |
| WO | WO 99/06355 A1 | | 2/1999 |
| WO | WO 99/06356 A1 | | 2/1999 |
| WO | WO 99/06357 A1 | | 2/1999 |
| WO | WO 99/52632 A1 | | 10/1999 |
| WO | WO 99/62855 A1 | | 12/1999 |
| WO | WO 99/64155 A1 | | 12/1999 |
| WO | WO 99/65506 A1 | | 12/1999 |
| WO | WO 01/36429 A1 | | 5/2001 |
| WO | WO 02/13964 A1 | | 2/2002 |
| WO | WO 02/30854 A2 | | 4/2002 |
| WO | WO 02/053527 A1 | | 7/2002 |
| WO | WO 03/011457 A1 | | 2/2003 |
| WO | WO 03/031392 A1 | | 4/2003 |
| WO | WO 03/068729 A1 | | 8/2003 |
| WO | WO 2004/007432 A1 | | 1/2004 |
| WO | WO 2004/007434 A1 | | 1/2004 |
| WO | WO 2004/060855 A1 | | 7/2004 |
| WO | WO 2004/065352 A1 | | 8/2004 |
| WO | WO 2004/087314 A1 | | 10/2004 |
| WO | WO 2009/092639 A1 | | 7/2009 |

OTHER PUBLICATIONS

International Search Report dated Jan. 25, 2010 issued in PCT/EP2009/062896.
International Search Report (PCT/ISN210) issued on May 25, 2010, by European Patent Office as the International Searching Authority for International Application No. PCT/EP2010/050521.
International Search Report dated Jul. 30, 2009 issued in PCT/EP 2009/050265.
Office Action mailed Jul. 5, 2012, in U.S. Appl. No. 12/864,101.
Office Action mailed Dec. 17, 2012, in U.S. Appl. No. 12/864,101.
Office Action mailed Jun. 28, 2013, in U.S. Appl. No. 12/864,101.
Final Office Action mailed Mar. 21, 2014, in U.S. Appl. No. 12/864,101.
Advisory Action mailed Jul. 30, 2014, in U.S. Appl. No. 12/864,101.
Office Action mailed Oct. 24, 2014, in U.S. Appl. No. 12/864,101.
Office Action mailed May 9, 2013, in U.S. Appl. No. 13/123,721.
Final Office Action mailed Nov. 14, 2013, in U.S. Appl. No. 13/123,721.
Office Action mailed Jun. 6, 2014, in U.S. Appl. No. 13/123,721.
Final Office Action mailed Nov. 17, 2014, in U.S. Appl. No. 13/123,721.
Office Action mailed Oct. 25, 2013, in U.S. Appl. No. 13/146,610.
Final Office Action mailed Jul. 17, 2014, in U.S. Appl. No. 13/146,610.
International Search Report dated Aug. 10, 2009, issued in PCT/EP2009/056917.

* cited by examiner

PREPARATION OF NITRILES FROM ETHYLENICALLY UNSATURATED COMPOUNDS

CROSS-REFERENCE TO PRIOR APPLICATIONS

This application is the U.S. National Stage of PCT/EP 2009/056916, filed Jun. 5, 2009 and designating the United States (published in the French language on Dec. 23, 2009, as WO 2009/153171 A1; the title and abstract were also published in English), and claims priority of FR 0803374, filed Jun. 17, 2008, each hereby expressly incorporated by reference in its entirety and each assigned to the assignee hereof.

The present invention relates to a process for the hydrocyanation of ethylenically unsaturated organic compounds to give compounds comprising at least one nitrile function.

It relates more particularly to the hydrocyanation of diolefins such as butadiene or of substituted olefins such as alkenenitriles, for instance pentenenitriles.

French Patent No. 1 599 761 describes a process for preparing nitriles by the addition of hydrocyanic acid to organic compounds having at least one ethylenic double bond, in the presence of a catalyst comprising nickel and an organophosphorus ligand, a triaryl phosphite. This reaction can be carried out in the presence or absence of a solvent.

When a solvent is used, it is preferably a hydrocarbon, such as benzene or xylenes, or a nitrile such as acetonitrile.

The catalyst used is an organic nickel complex, containing ligands such as phosphines, arsines, stibines, phosphites, arsenites or antimonites.

The presence of a promoter for activating the catalyst, such as a boron compound or a metal salt, generally a Lewis acid, is also recommended in said patent.

Many other catalytic systems have been proposed, generally comprising organophosphorus compounds belonging to the phosphite, phosphonite, phosphinite and phosphine family. These organophosphorus compounds may comprise one atom of phosphorus per molecule, and are described as monodentate ligands. They may comprise several phosphorus atoms per molecule, and they are then known as polydentate ligands; more particularly, ligands containing two phosphorus atoms per molecule (known as bidentate ligands) have been described in many patents.

However, the search for new catalytic systems which give greater performance levels, both in terms of catalytic activity and in terms of stability, is still ongoing.

One of the objectives of the present invention is to propose new catalytic systems which exhibit good catalytic activity in the hydrocyanation reaction, in particular the reaction for hydrocyanation of butadiene to adiponitrile.

To this effect, the present invention proposes a process for the hydrocyanation of a hydrocarbon-based compound comprising at least one ethylenic unsaturation, by reaction, in a liquid medium, with hydrogen cyanide in the presence of a catalytic system comprising a metal element chosen from transition metals and at least one organophosphorus ligand, characterized in that the catalytic system comprises, as organophosphorus ligand, a mixture of at least one monodentate organophosphite compound, and at least one monodentate organophosphine compound. The molar ratio of the monodentate organophosphite compound to the monodentate organophosphine compound is between 0.01 and 100.

According to one characteristic of the invention, the molar ratio relative to an atom of metal element, for the organophosphine compound, is between 0.1 and 10, and for the organophosphite compound, is between 0.1 and 10.

In a first embodiment of the invention, the molar ratio of the organophosphite compound to the organophosphine compound is advantageously between 1 and 100, preferably between 5 and 60.

In a second embodiment, the molar ratio of the organophosphite compound to the organophosphine compound is between 0.01 and 0.3.

According to another characteristic applicable to all the embodiments of the invention, the molar ratio between the sum of the moles of organophosphine and organophosphite compounds and the number of atoms of metal element is between 4 and 10.

The organophosphites suitable for the invention are in particular chosen from the group comprising triphenyl phosphite, ortho-tritolyl phosphite, para-tritlolyl phosphite and meta-tritolyl phosphite, and mixtures thereof.

The organophosphines suitable for the invention are in particular chosen from the group comprising the organophosphine compounds corresponding to general formula (I):

$$\left[ (R_1)_m \left\langle \bigcirc \right\rangle \right]_{3-n} P - Z_n \quad (I)$$

in which:

Z represents an aromatic or nonaromatic, substituted or unsubstituted, 5- or 6-atom cyclic group containing an oxygen, nitrogen or sulphur atom and such that the bond with the phosphorus is borne by the carbon in the alpha-position with respect to the heteroatom, n represents an integer from 0 to 3, m represents an integer from 0 to 5, the $R_1$ radical represents a hydrogen atom, a linear or branched alkyl radical, that may contain heteroatoms, having from 1 to twelve carbon atoms, a substituted or unsubstituted aromatic or cycloaliphatic radical that may comprise heteroatoms, a carbonyl, alkoxycarbonyl or alkoxy radical, a halogen atom, a nitrile group or a haloalkyl group having from one to twelve carbon atoms.

Z is preferably a furyl, thienyl, pyrryl or pyridyl group, and more preferably a furyl or thienyl group.

According to the invention, the composition of the catalytic system is illustrated by general formula (II) (this formula does not represent the structure of the compounds or complexes present in the catalytic system):

$$M[L_1]_t[L_2]_u \quad (II)$$

in which:

M is a transition metal, $L_1$ represents the organophosphite ligand, $L_2$ represents the organophosphine ligand, t and u, which may be identical or different, represent a number between 0.1 and 9.9 (limits included), the sum t+u being between 4 and 10.

The metals M which may be complexed by the organophosphorus ligands are, in general, all the transition metals of groups 1 b, 2b, 3b, 4b, 5b, 6b, 7b and 8 of the Periodic Table of Elements, as published in "Handbook of Chemistry and Physics, 51st Edition (1970-1971)" of The Chemical Rubber Company.

Among these metals, mention may more particularly be made of the metals that can be used as catalysts in hydrocyanation reactions. Thus, by way of nonlimiting examples, mention may be made of nickel, cobalt, iron, ruthenium, rhodium, palladium, osmium, iridium, platinum, copper, silver, gold, zinc, cadmium and mercury. Nickel is the preferred element for the hydrocyanation of unsaturated nitriles and olefins.

According to one particular embodiment of the invention, n in formula (I) represents 1 to 3.

According to another particular embodiment of the invention, n in formula (I) represents 0 and the $R_1$ radical represents a linear or branched alkyl radical, that may contain heteroatoms, having from 1 to twelve carbon atoms, a substituted or unsubstituted aromatic or cycloaliphatic radical that may comprise heteroatoms, a carbonyl, alkoxycarbonyl or alkoxy radical, a halogen atom, a nitrile group or a haloalkyl group having from one to twelve carbon atoms.

As suitable compounds of general formula (I), mention may be made, by way of nonlimiting examples, of tri(2-chlorophenyl)phosphine, tri(3-chlorophenyl)phosphine, tri(4-chlorophenyl)phosphine, (2-furyl)diphenylphosphine, di(2-furyl)phenylphosphine, tri(2-furyl)phosphine, (2-thienyl)diphenylphosphine, di(2-thienyl)phenylphosphine, tri(2-thienyl)phosphine, (2-pyrryl)diphenylphosphine, di(2-pyrryl)phenylphosphine, tri(2-pyrryl)phosphine, (2-pyridyl)diphenylphosphine, di(2-pyridyl)phenylphosphine and tri(2-pyridyl)phosphine.

For the preparation of the thienylphosphines and pyrrylphosphines according to general formula (I), reference may be made, for example, to the article by V. K. Issleib and A. Brack published in Zeitschrift für anorganische and allgemeine Chemie, 1957, 292, pages 245 to 253. For the synthesis of pyridylphosphines according to general formula (I), reference may be made, for example, to Patent EP0499328. For the use of furylphosphines in hydrocyanation, reference may be made, for example, to Patent WO 02/053527.

The preparation of the organometallic complexes comprising organophosphorus ligands that are suitable for the invention can be carried out by bringing a solution of a compound of the chosen metal, for example, nickel, into contact with a solution of the organophosphorus compound(s) of the invention.

The compound of the metal can be dissolved in a solvent. The metal can occur, in the compound used, either in the oxidation state that it will have in the organometallic complex, or in a higher oxidation state.

By way of example, it may be indicated that, in the organometallic complexes of the invention, rhodium is in the oxidation state (I), ruthenium in the oxidation state (II), platinum in the oxidation state (0), palladium in the oxidation state (0), osmium in the oxidation state (II), iridium in the oxidation state (I) and nickel in the oxidation state (0).

If, during the preparation of the organometallic complex, the metal is used in a higher oxidation state, it can be reduced in situ.

Among the complexes of metals M that can be used for the preparation of the organometallic complexes, mention may be made, by way of nonlimiting examples, of the following nickel compounds:

compounds in which the nickel is in the zero oxidation state, such as potassium tetracyanonickelate $K_4[Ni(CN)_4]$, bis(acrylonitrile)nickel(0), bis(1,5-cyclooctadiene)nickel (also known as $Ni(cod)_2$) and derivatives comprising ligands, such as tetrakis(triphenylphosphine)nickel(0);

nickel compounds, such as carboxylates (in particular the acetate), carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, arylsulphonates and alkylsulphonates.

When the nickel compound used corresponds to an oxidation state of the nickel of greater than 0, a reducing agent for nickel which reacts preferentially with the latter under the reaction conditions is added to the reaction medium. This reducing agent may be organic or inorganic. As nonlimiting examples, mention may be made of borohydrides, such as $NaBH_4$ or $KBH_4$, Zn powder, magnesium or hydrogen.

When the nickel compound used corresponds to the 0 oxidation state of nickel, it is also possible to add a reducing agent of the type of those mentioned above, but this addition is not essential.

When an iron compound is used, the same reducing agents are suitable. In the case of palladium, the reducing agents may in addition be components of the reaction medium (phosphine, solvent, olefin).

The organic compounds comprising at least one ethylenic double bond more particularly used in the present process are diolefins, such as butadiene, isoprene, 1,5-hexadiene or 1,5-cyclooctadiene, ethylenically unsaturated aliphatic nitriles, particularly linear pentenenitriles, such as 3-pentenenitrile or 4-pentenenitrile, monoolefins, such as styrene, methylstyrene, vinylnaphthalene, cyclohexene or methylcyclohexene, and mixtures of several of these compounds.

The pentenenitriles may contain, in addition to the 3-pentenenitrile and the 4-pentenenitrile, amounts, generally minor amounts, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, for example originating from the hydrocyanation reaction of butadiene to give unsaturated nitriles.

Specifically, during the hydrocyanation of butadiene, not insignificant amounts of 2-methyl-3-butenenitrile and of 2-methyl-2-butenenitrile are formed with the linear pentenenitriles.

The catalytic system used for the hydrocyanation according to the process of the invention can be prepared before it is introduced into the reaction medium, for example by addition to the organophosphorus compounds, alone or dissolved in a solvent, of the appropriate amount of compound of the chosen transition metal and, optionally, of the reducing agent. It is also possible to prepare the catalytic system "in situ" by simple addition of the organophosphorus compounds and of the compound of the transition metal to the hydrocyanation reaction medium, before or after the addition of the compound to be hydrocyanated.

The amount of nickel compound or of compound of another transition metal used is chosen in order to obtain a concentration, as moles of transition metal per mole of organic compounds to be hydrocyanated or isomerized, of between $10^{-4}$ and 1, and preferably between 0.005 and 0.5 mol of nickel or of the other transition metal used.

The amount of organophosphorus compounds used to form the catalytic system is chosen such that the number of moles of these compounds relative to 1 mol of transition metal is from 0.5 to 100 and preferably from 2 to 50.

Although the reaction is generally carried out without solvent, it may be advantageous to add an inert organic solvent. The solvent can be a solvent for the catalyst which is miscible with the phase comprising the compound to be hydrocyanated at the hydrocyanation temperature. By way of examples of such solvents, mention may be made of aromatic, aliphatic or cycloaliphatic hydrocarbons.

The hydrocyanation reaction is generally carried out at a temperature of 10° C. to 200° C., and preferably of 30° C. to 120° C. It can be carried out in a single-phase medium.

The process of the invention can be carried out continuously or batchwise.

The hydrogen cyanide used can be prepared from metal cyanides, in particular sodium cyanide, or cyanohydrins, such as acetone cyanohydrin, or by any other known synthetic process, such as the Andrussov process which consists in reacting methane with ammonia and air.

The hydrogen cyanide, free of water, is introduced into the reactor in the gaseous form or in the liquid form. It can also be dissolved beforehand in an organic solvent.

In the context of a batchwise implementation, it is possible in practice to charge, to a reactor purged beforehand using an inert gas (such as nitrogen or argon), either a solution containing all or a portion of the various constituents, such as the organophosphorus compounds suitable for the invention, the transition metal (nickel) compound, the optional reducing agent and the optional solvent, or said constituents separately. Generally, the reactor is then brought to the chosen temperature, and the compound to be hydrocyanated is then introduced. The hydrogen cyanide is then itself introduced, preferably continuously and uniformly.

When the reaction (the progress of which can be monitored by assaying withdrawn samples) is complete, the reaction mixture is withdrawn after cooling and the reaction products are isolated and separated, for example by distillation.

Advantageously, the synthesis of dinitriles, such as adiponitrile, from diolefins (butadiene) is obtained in two successive stages. The first stage consists in hydrocyanating a double bond of the diolefin so as to obtain an unsaturated mononitrile. The second stage consists in hydrocyanating the unsaturation of the mononitrile so as to obtain the corresponding dinitrile(s). These two stages are generally carried out with a catalytic system comprising an organometallic complex of the same nature. However, the organophosphorus compound/metal element ratios and concentration of the catalyst may be different. In addition, it is preferable to combine a cocatalyst or promoter with the catalytic system in the second stage. This cocatalyst or promoter is generally a Lewis acid.

The Lewis acid used as cocatalyst makes it possible, in particular, in the case of hydrocyanation of ethylenically unsaturated aliphatic nitriles, to improve the linearity of the dinitriles obtained, i.e. the percentage of linear dinitrile relative to all the dinitriles formed, and/or to increase the activity and the lifetime of the catalyst.

The term "Lewis acid" is intended to mean, in the present text, according to the usual definition, compounds which accept electron pairs.

Use may in particular be made of the Lewis acids mentioned in the book edited by G. A. Olah, "Friedel-Crafts and related Reactions", volume I, pages 191 to 197 (1963).

The Lewis acids which can be used as cocatalysts in the present process are chosen from the compounds of elements from groups Ib, IIb, IIIa, IIIb, IVa, IVb, Va, Vb, VIb, VIIb and VIII of the Periodic Table of Elements. These compounds are most commonly salts, in particular halides, such as chlorides or bromides, sulphates, sulphonates, halosulphonates, perhaloalkylsulphonates, in particular fluoroalkylsulphonates or perfluoroalkylsulphonates, carboxylates and phosphates.

By way of nonlimiting examples of such Lewis acids, mention may be made of zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, chlorides or bromides of rare earth elements, such as lanthanum, cerium, praseodymium, neodymium, samarium, europium, gadolinium, terbium, dysprosium, hafnium, erbium, thallium, ytterbium and lutetium, cobalt chloride, ferrous chloride, yttrium chloride, or the compounds described in the unpublished French Patent Application filed on 25 Jan. 2008 under No. 08 00381.

Use may also be made, as Lewis acid, of organometallic compounds such as triphenylborane or titanium isopropoxide.

It is, of course, possible to use mixtures of several Lewis acids.

Among Lewis acids, preference is most particularly given to zinc chloride, zinc bromide, stannous chloride, stannous bromide, triphenylborane, and zinc chloride/stannous chloride mixtures.

The Lewis acid cocatalyst used generally represents from 0.01 to 50 mol per mole of transition metal compound, more particularly of nickel compound, and preferably from 1 to 10 mol per mole.

The unsaturated mononitriles used in this second stage are advantageously linear pentenenitriles, such as 3-pentenenitrile or 4-pentenenitrile, and mixtures thereof.

These pentenenitriles may contain amounts, generally minor amounts, of other compounds, such as 2-methyl-3-butenenitrile, 2-methyl-2-butenenitrile or 2-pentenenitrile.

The catalytic solution used for the hydrocyanation in the presence of a Lewis acid can be prepared before it is introduced into the reaction medium, for example by simple mixing of the organophosphorus compounds, of the appropriate amount of compound of the transition metal chosen, of the Lewis acid and, optionally, of the reducing agent. It is also possible to prepare the catalytic solution "in situ" by addition of these various constituents to the reaction medium.

It is also possible, under the conditions of the hydrocyanation process of the present invention, and in particular by performing the procedure in the presence of the catalytic system described above comprising at least the mixture of organophosphorus compounds in accordance with the invention and at least one compound of a transition metal, to carry out, in the absence of hydrogen cyanide, the isomerization of 2-methyl-3-butenenitrile to give pentenenitriles, and more generally of branched unsaturated nitriles to give linear unsaturated nitriles.

The 2-methyl-3-butenenitrile subjected to the isomerization according to the invention can be used alone or as a mixture with other compounds. Thus, 2-methyl-3-butenenitrile can be introduced as a mixture with 2-methyl-2-butenenitrile, 4-pentenenitrile, 3-pentenenitrile, 2-pentenenitrile or butadiene.

It is particularly advantageous to treat the reaction mixture originating from the hydrocyanation of butadiene with HCN in the presence of the catalytic system in accordance with the invention. In the context of this preferred variant, since the catalytic system is already present for the butadiene hydrocyanation reaction, it is sufficient to halt any introduction of hydrogen cyanide in order to allow the isomerization reaction to take place. It is possible, if appropriate, in this variant, to carry out a gentle flushing of the reactor using an inert gas, such as nitrogen or argon, for example, in order to drive off the hydrocyanic acid which might still be present.

The isomerization reaction is generally carried out at a temperature of 10° C. to 200° C., and preferably of 60° C. to 140° C.

In the preferred case of an isomerization immediately following the butadiene hydrocyanation reaction, it will be advantageous to carry out the reaction at a temperature at which the hydrocyanation was carried out, or slightly higher.

As for the process for the hydrocyanation of ethylenically unsaturated compounds, the catalytic system used for the isomerization can be prepared before it is introduced into the reaction medium, for example by mixing the organophosphorus compounds, the appropriate amount of compound of the chosen transition metal and, optionally, of the reducing agent. It is also possible to prepare the catalytic system "in situ" by addition of these various constituents to the reaction medium. The amount of transition metal compound, and more particularly nickel compound, used, and also the amount of organophosphorus compounds, are the same as for the hydrocyanation reaction.

Although the isomerization reaction is generally carried out without solvent, it can be advantageous to add an inert organic solvent that can be subsequently used as extraction solvent. This is in particular the case when such a solvent was used in the reaction for hydrocyanation of butadiene used to prepare the medium subjected to the isomerization reaction. Such solvents can be chosen from those that were mentioned above for the hydrocyanation.

However, the preparation of dinitrile compounds by hydrocyanation of an olefin such as butadiene can be carried out using a catalytic system in accordance with the invention for the stages of formation of the unsaturated nitriles and the stage of isomerization above, it being possible for the reaction for the hydrocyanation of the unsaturated nitriles to give dinitriles to be carried out with a catalytic system in accordance with the invention or any other catalytic system already known for this reaction.

Likewise, the reaction for the hydrocyanation of the olefin to give unsaturated nitriles and the isomerization of the latter can be carried out with a catalytic system different from that of the invention, the stage of hydrocyanation of the unsaturated nitriles to give dinitriles being carried out with a catalytic system in accordance with the invention.

Other details and advantages of the invention will be illustrated by the examples given below, only by way of indication and which are not limiting in nature.

ABBREVIATIONS USED cod: cyclooctadiene
Ni(cod)$_2$: bis(1,5-cyclooctadiene)nickel
3PN: 3-pentenenitrile
AdN: adiponitrile
ESN: ethylsuccinonitrile
MGN: methylglutaronitrile
DN: dinitrile compounds (AdN, MGN or ESN)
TIBAO: tetraisobutyldialuminoxane
Mes: mesityl group (2,4,6-trimethylphenyl)
Ph: phenyl group
TTP: tritolyl phosphite
TPP: triphenyl phosphite
RY(DN): real yield of dinitriles corresponding to the ratio of the number of moles of dinitriles formed to the number of moles of 3PN introduced
Linearity (L): ratio of the number of moles of AdN formed to the number of moles of dinitriles formed (sum of the moles of AdN, ESN and MGN).

The following compounds: 3PN, Ni(cod)$_2$, ZnCl$_2$, TTP, TPP, tris(2-thienyl)phosphine, tris(2-furyl)phosphine and tris(4-chlorophenyl)phosphine are known products that are available.

EXAMPLES 1 TO 12

Hydrocyanation of 3-PN to give AdN

The tests are carried out according to the following procedure:

The following are successively charged, under an argon atmosphere, to a 60 ml glass tube of Shott type, equipped with a septum stopper:

ligand 1 (see table 1 for nature and amount)
ligand 2 (see table 1 for nature and amount)
1.21 g (15 mmol, 30 equivalents) of 3PN
138 mg (0.5 mmol, 1 equivalent) of Ni(cod)$_2$
62 mg (0.5 mmol, 1 equivalent) of ZnCl$_2$.

The mixture is brought to 70° C. with stirring. Acetone cyanohydrin is fed into the reaction medium via a syringe driver at a flow rate of 0.45 ml per hour. After injecting for 3 hours, the syringe driver is stopped. The mixture is cooled to ambient temperature, diluted with acetone, and analysed by gas chromatography.

In these examples, the phosphine ligands used have formulae III to V below:

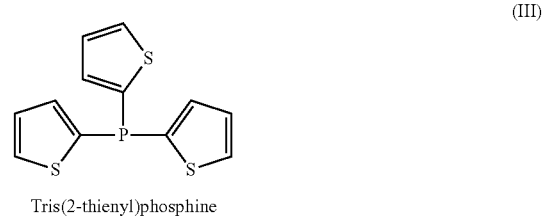

Tris(2-thienyl)phosphine (III)

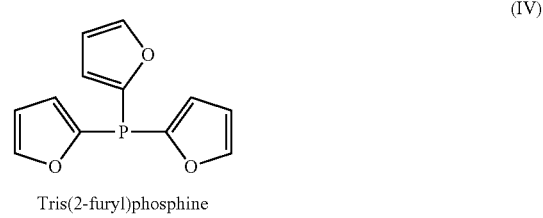

Tris(2-furyl)phosphine (IV)

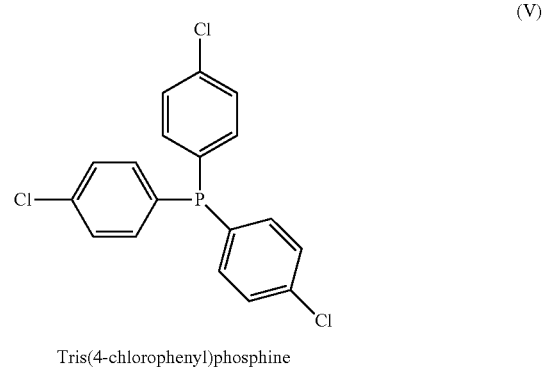

Tris(4-chlorophenyl)phosphine (V)

The results are collated in Table 1 below:

TABLE 1

Examples 1 to 14

| Example | Ligand 1 | Ligand 2 | Ligand1/Ligand2/Ni (molar equivalents) | Linearity (L) | RY (DN) |
|---|---|---|---|---|---|
| 1 (comparative) | TTP | — | 5/0/1 | 82.4 | 58.5 |
| 2 (comparative) | Tris(2-thienyl)phosphine | — | 5/0/1 | 62.5 | 75.8 |
| 3 (comparative) | Tris(4-chlorophenyl)-phosphine | — | 5/0/1 | 60 | 64.8 |
| 4 (comparative) | Tris(2-furyl)phosphine | — | 5/0/1 | 64.6 | 78.4 |
| 5 | Tris(2-thienyl)phosphine | TTP | 1/4/1 | 77.3 | 71.5 |
| 6 | Tris(2-thienyl)phosphine | TTP | 2.5/2.5/1 | 72.8 | 75.9 |
| 7 | Tris(2-thienyl)phosphine | TTP | 4/1/1 | 67.8 | 79.3 |
| 8 | Tris(4-chlorophenyl)-phosphine | TTP | 2.5/2.5/1 | 75.9 | 67.2 |
| 9 | Tris(2-furyl)phosphine | TTP | 2.5/2.5/1 | 67.3 | 80.7 |
| 10 | Tris(2-thienyl)phosphine | TTP | 0.1/4.9/1 | 82.6 | 64.5 |
| 11 | Tris(4-chlorophenyl)-phosphine | TTP | 0.1/4.9/1 | 82.6 | 62.2 |
| 12 | Tris(2-furyl)phosphine | TTP | 0.1/4.9/1 | 81.6 | 62.8 |
| 13 (comparative) | TPP | — | 5/0/1 | 81.9 | 33.8 |
| 14 | Tris(2-thienyl)phosphine | TPP | 0.1/4.9/1 | 80.7 | 38.5 |

The invention claimed is:

1. A process for the hydrocyanation of a hydrocarbon-based compound having at least one site of ethylenic unsaturation, said process comprising: reacting said hydrocarbon-based compound with hydrogen cyanide in a liquid medium in the presence of a catalytic system;

said catalytic system comprising a transition metal and at least one organophosphorus ligand which forms a complex with said transition metal, wherein said catalytic system comprises as said organophosphorus ligand at least one monodentate organophosphite compound and at least one monodentate organophosphine compound;

wherein the at least one organophosphite compound is selected from the group consisting of ortho-tritolyl phosphite, para-tritolyl phosphite, meta-tritolyl phosphite, and mixtures thereof; and the at least one organophosphine compound has the formula (I):

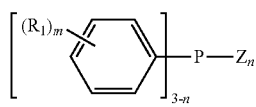

in which:

Z is an aromatic or non-aromatic, substituted or unsubstituted, 5- or 6-atom cyclic moiety containing an oxygen, nitrogen or sulfur atom and the bond with the phosphorus atom is borne by the carbon in the alpha-position with respect to the heteroatom, n is an integer ranging from 0 to 3, m is an integer ranging from 0 to 5, and $R_1$ is a hydrogen atom, a linear or branched alkyl radical, that may contain heteroatoms, having from 1 to 12 carbon atoms, a substituted or unsubstituted aromatic or cycloaliphatic radical that may comprise heteroatoms, a carbonyl, alkoxycarbonyl or alkoxy radical, a halogen atom, a nitrile group or a haloalkyl radical having from 1 to 12 carbon atoms, and when, in formula (I), n is 0, m is an integer ranging from 1-5, $R_1$ is a linear or branched alkyl radical, that may contain heteroatoms, having from 1 to 12 carbon atoms, a substituted or unsubstituted aromatic or cycloaliphatic radical that may comprise heteroatoms, a carbonyl, alkoxycarbonyl or alkoxy radical, a halogen atom, a nitrile group or a haloalkyl radical having from 1 to 12 carbon atoms, wherein: (a) the molar ratio of said organophosphine compound to an atom of said transition metal is from 0.1 to 10, (b) the molar ratio of said monodentate organophosphite compound to an atom of said transition metal is from 0.1 to 10, and (c) the molar ratio of the organophosphite compound to the organophosphine compound is from 0.01 to 100.

2. The process as defined by claim 1, wherein the molar ratio of the organophosphite compound to the organophosphine compound ranges from 1 to 100.

3. The process as defined by claim 1, wherein the molar ratio of the organophosphite compound to the organophosphine compound ranges from 0.01 to 0.3.

4. The process as defined by claim 1, wherein the molar ratio of the sum of the moles of organophosphine and organophosphite compounds to the number of atoms of metal element ranges from 4 to 10.

5. The process as defined by claim 1, where, in formula (I), n is an integer ranging from 1 to 3.

6. The process as defined by claim 1, where, in formula (I), Z is a furyl, thienyl, pyrryl or pyridyl radical.

7. The process as defined by claim 1, wherein the at least one compound of general formula I comprises one of the formulae III to V below:

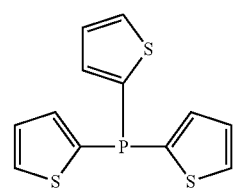

(III)

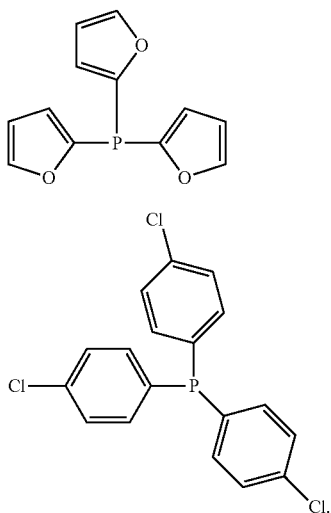

8. The process as defined by claim 1, wherein the transition metal is selected from the group consisting of nickel, cobalt, iron, ruthenium, rhodium, palladium, osmium, iridium, platinum, copper, silver, gold, zinc, cadmium and mercury.

9. The process as defined by claim 1, wherein said catalytic system has the formula (II):

$$M[L_1]_t[L_2]_u \quad (II)$$

in which:
M is a transition metal,
$L_1$ is an organophosphite ligand,
$L_2$ is an organophosphine ligand,
t and u, which may be identical or different, are each a number ranging from 0.1 to 9.9 (limits included), and the sum t+u ranges from 4 to 10.

10. The process as defined by claim 1, wherein the organic compound having at least one ethylenic double bond is selected from the group consisting of diolefins, ethylenically unsaturated aliphatic nitriles, monoolefins, styrene, methylstyrene, vinylnaphthalene, cyclohexene, methylcyclohexene, and mixtures thereof.

11. The process as defined by claim 1, wherein the amount of said transition metal is selected such that from $10^{-4}$ to 1 mol of said transition metal is present per mole of said hydrocarbon-based compound having at least one site of ethylenic unsaturation, and the amount of organophosphorus compounds (total of said at least one monodentate organophosphite compound and said at least one monodentate organophosphine compound) present is selected such that the number of moles of these compounds relative to 1 mol of transition metal ranges from 0.5 to 100.

12. The process as defined by claim 1, wherein an ethylenically unsaturated nitrile is reacted with hydrogen cyanide, in the presence of a catalytic system comprising at least one compound of a transition metal, at least one monodentate organophosphite compound and at least one monodentate organophosphine compound, and a co-catalyst comprising at least one Lewis acid, to form a dinitrile.

13. The process as defined by claim 12, wherein the ethylenically unsaturated nitrile compound is selected from the group consisting of ethylenically unsaturated aliphatic nitriles comprising linear pentenenitriles, 3-pentenenitrile, 4-pentenenitrile, and mixtures thereof.

14. The process as defined by claim 12, wherein the Lewis acid co-catalyst is selected from the group consisting of compounds of elements from Groups Ib, IIb, IIIa, IIIb, IVa, IVb, Va, Vb, VIb, VIIb and VIII of the Periodic Table of Elements.

15. The process as defined by claim 12, wherein the Lewis add is selected from the group consisting of zinc chloride, zinc bromide, zinc iodide, manganese chloride, manganese bromide, cadmium chloride, cadmium bromide, stannous chloride, stannous bromide, stannous sulfate, stannous tartrate, indium trifluoromethylsulphonate, chlorides and bromides of rare earth elements selected from the group consisting of lanthanum, cerium, praseodymium, neodymium, samarium, europium, gadolinium, terbium, dysprosium, hafnium, erbium, thallium, ytterbium, and lutetium, cobalt chloride, ferrous chloride, yttrium chloride, organometallic compounds, and mixtures thereof.

16. The process as defined by claim 1, wherein when said hydrocarbon-based compound having at least one site of ethylenic unsaturation is butadiene, and 2-methyl-3-butenenitrile is formed In a reaction mixture from the hydrocyanation of butadiene, the process further comprises isomerizing 2-methyl-3-butenenitrile in the absence of hydrogen cyanide, but In the presence of a catalytic system comprising a transition metal, at least one monodentate organophosphite compound and at least one monodentate organosphosphine compound.

17. The process as defined by claim 1, wherein the organic compound having at least one ethylenic double bond is selected from the group consisting of butadiene, isoprene, 1,5-hexadiene, 1,5-cyclooctadiene, 3-pentenenitrile, 4-pentenenitrile, and mixtures thereof.

18. The process of claim 15 wherein the organometallic compound is triphenylborane or titanium isopropoxide.

19. The process as defined by claim 1, wherein the transition metal is nickel.

* * * * *